United States Patent
Liu et al.

(10) Patent No.: US 9,321,995 B2
(45) Date of Patent: Apr. 26, 2016

(54) STEM CELL CULTURE MEDIUM AND ITS APPLICATIONS AS WELL AS A STEM CELL CULTURE METHOD

(71) Applicant: SHANGHAI TENTH PEOPLE'S HOSPITAL, Shanghai (CN)

(72) Inventors: Xiaoqing Liu, Shanghai (CN); Ming Ying, Shanghai (CN); Guangfeng Chen, Shanghai (CN); Longpo Zheng, Shanghai (CN)

(73) Assignee: SUZHOU BIOWISETECH CO., LTD., Suzhou (CN)

( * ) Notice: Subject to any disclaimer, the term of this patent is extended or adjusted under 35 U.S.C. 154(b) by 257 days.

(21) Appl. No.: 13/885,000

(22) PCT Filed: Jan. 31, 2013

(86) PCT No.: PCT/CN2013/071173
§ 371 (c)(1),
(2) Date: May 13, 2013

(87) PCT Pub. No.: WO2014/094386
PCT Pub. Date: Jun. 26, 2014

(65) Prior Publication Data
US 2014/0178987 A1    Jun. 26, 2014

(30) Foreign Application Priority Data

Dec. 20, 2012    (CN) .......................... 2012 1 0557941

(51) Int. Cl.
*C12N 5/00*    (2006.01)
*C12N 5/0775*    (2010.01)

(52) U.S. Cl.
CPC ............ *C12N 5/0667* (2013.01); *C12N 5/0663* (2013.01); *C12N 5/0665* (2013.01);
(Continued)

(58) Field of Classification Search
None
See application file for complete search history.

(56) References Cited

U.S. PATENT DOCUMENTS 5,908,782 A * 6/1999 Marshak et al. .............. 435/366
7,109,032 B2 * 9/2006 Cancedda et al. ............ 435/404

FOREIGN PATENT DOCUMENTS

| CN | 101984051 A | 3/2011 |
| CN | 102399742 A | 4/2012 |
| CN | 102719393 A | 10/2012 |
| CN | 102827807 A | 12/2012 |
| CN | 102827810 A | 12/2012 |

OTHER PUBLICATIONS

The World Intellectual Property Organization (WIPO) International Search Report for PCT/CN2013/071173 Oct. 3, 2013.

* cited by examiner

*Primary Examiner* — Blaine Lankford
(74) *Attorney, Agent, or Firm* — Anova Law Group, PLLC (57) ABSTRACT

The present invention discloses a stem cell culture medium and its applications as well as a stem cell culture method. The said stem cell culture medium contains no serum. The said stem cell culture medium contains amino acids, vitamins, salts, lipids, cytokines and protein polypeptides. The said stem cell culture medium is suitable for rapid culture of stem cells derived from human and mammalian tissues, including but not limited to, adipose mesenchymal stem cells, bone marrow mesenchymal stem cells and umbilical cord blood stem cells. The said culture medium can increase the proliferation speed of the stem cells 3-5 times, without any affects on their differentiation potentials. Comparing the said stem cell culture medium to a routine culture medium, the said culture medium is not only able to proliferate stem cells derived from different sources more rapidly and achieve more proliferation generations, but also keep their differentiation potentials well.

12 Claims, 4 Drawing Sheets

(52) U.S. Cl.
CPC ......... *C12N2500/32* (2013.01); *C12N 2500/33* (2013.01); *C12N 2500/36* (2013.01); *C12N 2500/38* (2013.01); *C12N 2500/90* (2013.01); *C12N 2501/105* (2013.01); *C12N 2501/11* (2013.01); *C12N 2501/113* (2013.01); *C12N 2501/115* (2013.01); *C12N 2501/125* (2013.01); *C12N 2501/135* (2013.01); *C12N 2501/165* (2013.01); *C12N 2501/235* (2013.01); *C12N 2501/39* (2013.01); *C12N 2501/91* (2013.01)

STEM CELL CULTURE MEDIUM AND ITS APPLICATIONS AS WELL AS A STEM CELL CULTURE METHOD

TECHNICAL FIELD

The present invention relates to the field of cell culture, and more particularly to a stem cell culture medium and its applications as well as a stem cell culture method.

BACKGROUND ART

Many studies have shown that stem cells are self-renewable, can differentiate into other functional cells under the right conditions, thus the stem cells could be effective for the treatment of difficult human diseases. However, a normal mature tissue contains very little stem cells. So how to rapidly proliferate and culture stem cells in vitro becomes an important technique in studying the action mechanisms of stem cells and exploring their application methods in treating human diseases.

Although stem cells are in a very small amount, they are widely distributed in various mammalian tissues and organs, including but not limited to, bone marrow, umbilical cord, adipose tissues, brain, retina, heart, liver, lung and skin. Many studies have shown that, the low amount of stem cells can be further proliferated by appropriate methods in vitro. The most routine culture medium used to culture stem cells is a culture medium with some fetal calf serum. However, the stem cells cultured in this kind of medium, are not only growing slowly, but their differentiation potential into functional cells is also greatly reduced after proliferating over 5 generations, and the potential non-reproducibility between different bovine serum batches also greatly affect its large scale applications. On the other hand, bovine serum is heterologous to human, which limits its clinic applications. Therefore, it is an important research topic for exploring the culture conditions for stem cells rapid proliferation without affecting their differentiation potentials as well as optimizing the compositions of their culture medium.

BRIEF SUMMARY OF THE INVENTION

In view of the defects in prior art, the present invention aims to provide a stem cell culture medium and its applications as well as a stem cell culture method, in order to solve the problem that stem cells grow slowly in current culture medium with bovine serum, and the problem of the decline of differentiation potentials after the cell proliferation times increase.

The technical solution of the present invention is as follows:

A stem cell culture medium, wherein, the said stem cell culture medium contains no serum, instead, it contains amino acids, vitamins, salts, lipids, cytokines and protein polypeptides, wherein, the said amino acids include alanine, arginine, asparagine, aspartic acid, cysteine, glutamic acid, glycine, histidine, isoleucine, leucine, lysine, methionine, phenylalanine, proline, serine, threonine, tryptophan, tyrosine, valine and glutamine;

The said cytokines and protein polypeptides include fibroblast growth factor-1, (fibroblast growth factor-2, epidermal growth factor, platelet-derived growth factor, insulin, insulin-like growth factor-1, vascular endothelial growth factor, placenta growth factor, leukocyte inhibitor factor, stem cell factors, transferrin and human serum albumin;

The said vitamins includes biotin, choline chloride, D-pantothenic acid sodium, folic acid, inositol, niacinamide, pyridoxine hydrochloride, riboflavin, thiamine hydrochloride, coenzyme Q10, vitamin B12, putrescine dihydrochloride, vitamin C and vitamin E;

The said lipids include dexamethasone, oleic acid, cholesterol, monoethanolamine, linoleic acid, lipoic acid and lipid mixtures;

The said salts include sodium bicarbonate, calcium chloride, potassium chloride, magnesium chloride, magnesium sulfate, sodium chloride, sodium dihydrogen phosphate monohydrate, sodium phosphate dibasic and sodium pyruvate;

The said stem cell culture medium also includes antioxidant, D-glucose, taurine and heparin sodium.

The said stem cell culture medium, counted in 1 liter, wherein, it comprises the following components:

| Component | Amount |
|---|---|
| Alanine | 0.01~0.25 mM |
| Arginine | 0.4~10 mM |
| Asparagine | 0.11~2.75 mM |
| Aspartic acid | 0.03~0.75 mM |
| Cysteine | 0.03~0.75 mM |
| Glutamic acid | 0.03~0.75 mM |
| Glycine | 0.05~1.25 mM |
| Histidine | 0.03~0.75 mM |
| Isoleucine | 0.5~12.5 mM |
| Leucine | 0.24~6 mM |
| Lysine | 0.2~5 mM |
| Methionine | 0.12~3 mM |
| Phenylalanine | 0.21~5.25 mM |
| Proline | 0.004~0.1 mM |
| Serine | 0.15~3.5 mM |
| Threonine | 0.06~1.5 mM |
| Tryptophan | 0.02~0.5 mM |
| Tyrosine | 0.03~0.75 mM |
| Valine | 0.28~7 mM |
| Glutamine | 0.8~20 mM |
| Epidermal growth factor | 1-10 µg/L |
| Fibroblast growth factor | 11-10 µg/L |
| Fibroblast growth factor2 | 1-10 µg/L |
| Insulin-like growth factor 1 | 1-10 µg/L |
| Leukocyte inhibitor factor | 1-10 µg/L |
| Platelet derived growth factor | 1-10 µg/L |
| Placenta growth factor | 1-10 µg/L |
| Stem cell factor | 1-10 µg/L |
| Vascular endothelial growth factor | 1-10 µg/L |
| Insulin | 1~25 mg/L |
| Transferrin | 4~100 mg/L |
| Human serum albumin | 0.02~0.5 g/L |
| Biotin | 6~150 µM |
| Choline chloride | 12~300 µM |
| Folic acid | 1.2~30 µM |
| Coenzyme Q10 | 0.2~5 µM |
| Dexamethasone | 2~50 nM |
| D-pantothenic acid sodium | 1~25 µM |
| Inositol | 14-350 µM |
| Nicotinamide | 4~100 µM |
| Pyridoxine hydrochloride | 0.03~0.75 µM |
| Riboflavin | 0.11~2.75 µM |
| Thiamine hydrochloride | 0.11~2.75 µM |
| Vitamin B12 | 0.1~2.5 µM |
| Putrescine dihydrochloride | 0.1~2.5 µM |
| Vitamin C | 2~50 mg/L |
| Vitamin E | 0.05~1.25 mg/L |
| Heparin sodium | 0.08~2 g/L |
| D-glucose | 3.6~90 mM |
| Reduced glutathione | 0.0002~0.005 mg/L |
| Taurine | 0.00144~0.36 g/L |
| β-mercaptoethanol | 0.01~0.25 µg/L |
| Phenol red | 1.62~40.5 mg/L |
| Oleic acid | 0.5~12.5 mg/L |
| Linoleic acid | 0.5~7.5 mg/L |
| Lipoic acid | 0.02~0.5 mg/L |
| Lipid mixtures | 0.2~5 ml/L |
| Cholesterol | 1~25 mg/L |

-continued

| | |
|---|---|
| Ethanolamine | 12~300 µl/L |
| Sodium bicarbonate | 11.6 mM |
| Calcium chloride | 0.084 mM |
| Potassium chloride | 4.16 mM |
| Magnesium chloride | 0.3 mM |
| Magnesium sulfate | 0.407 mM |
| Sodium chloride | 120.61 mM |
| Sodium dihydrogen phosphate monohydrate | 0.453 mM |
| Sodium phosphate dibasic | 0.5 mM |
| Sodium pyruvate | 0.1~2.5 mM |

The said stem cell culture medium, counted in 1 liter, wherein, it comprises the following components:

| | |
|---|---|
| Alanine | 0.05 mM |
| Arginine | 2 mM |
| Asparagine | 0.55 mM |
| Aspartic acid | 0.4 mM |
| Cysteine | 0.15 mM |
| Glutamic acid | 0.15 mM |
| Glycine | 0.25 mM |
| Histidine | 0.15 mM |
| Isoleucine | 2.50 mM |
| Leucine | 1.20 mM |
| Lysine | 1.00 mM |
| Methionine | 0.60 mM |
| Phenylalanine | 1.05 mM |
| Proline | 0.02 mM |
| Serine | 0.70 mM |
| Threonine | 0.30 mM |
| Tryptophan | 0.10 mM |
| Tyrosine | 0.15 mM |
| Valine | 1.4 mM |
| Glutamine | 4 mM |
| Sodium bicarbonate | 11.6 mM |
| Calcium chloride | 0.084 mM |
| Potassium chloride | 4.16 mM |
| Magnesium chloride | 0.3 mM |
| Magnesium sulfate | 0.407 mM |
| Sodium chloride | 120.61 mM |
| Sodium dihydrogen phosphate monohydrate | 0.453 mM |
| Sodium phosphate dibasic | 0.5 mM |
| Insulin | 5 mg/L |
| Transferrin | 20 mg/L |
| Human serum albumin | 0.1 g/L |
| Biotin | 30 µM |
| Choline chloride | 60 µM |
| Folic acid | 6 µM |
| Coenzyme Q10 | 1 µM |
| DXM (Dexamethasone) | 10 nM |
| D-pantothenic acid sodium | 5 µM |
| Inositol | 70 µM |
| Nicotinamide | 20 µM |
| Pyridoxine hydrochloride | 0.15 µM |
| Riboflavin | 0.55 µM |
| Thiamine hydrochloride | 0.55 µM |
| Vitamin B12 | 0.5 µM |
| Putrescine dihydrochloride | 0.5 µM |
| Vitamin C | 10 mg/L |
| Vitamin E | 0.25 mg/L |
| Heparin sodium | 0.4 g/L |
| D-glucose | 18 mM |
| Reduced glutathione | 0.001 mg/L |
| Taurine | 0.0072 g/L |
| β-mercaptoethanol | 0.05 µg/L |
| Phenol red | 8.1 mg/L |
| Oleic acid | 2.5 mg/L |
| Linoleic acid | 1.5 mg/L |
| Lipoic acid | 0.1 mg/L |
| Lipid mixtures | 1 ml/L |
| Cholesterol | 5 mg/L |
| Ethanolamine | 60 µl/L |
| Sodium bicarbonate | 11.6 mM |
| Calcium chloride | 0.084 mM |
| Potassium chloride | 4.16 mM |

-continued

| | |
|---|---|
| Magnesium chloride | 0.3 mM |
| Magnesium sulfate | 0.407 mM |
| Sodium chloride | 120.61 mM |
| Sodium dihydrogen phosphate | 0.453 mM |
| Disodium hydrogen phosphate | 0.5 mM |
| Sodium pyruvate | 0.5 mM |

An application of the said stem cell culture medium, wherein, the said stem cell culture medium is used for culturing stem cells.

The application of the said stem cell culture medium, wherein, the said stem cells include but not limited to human and mammalian cells.

The application of the said stem cell culture medium, wherein, the said stem cells are isolated from various tissues or organs. The said tissues and organs include, but not limited to, the bone marrow, umbilical cord, adipose tissue, brain tissue, retina, heart, liver, lung and skin.

A stem cell culture method using the said stem cell culture medium, wherein, before culturing the stem cells, materials promoting cell adhesion are coated onto the plate, followed by adding the stem cell culture medium and stem cells in sequence.

The said stem cell culture method, wherein, the said materials applied to promote stem cells adhesive, are collagen, gelatin, polylysine, fibronectin, laminin, vibronectin or their mixtures.

Benefits: the said stem cell culture medium contains no serum, is suitable for rapid culture of stem cells derived from human and mammalian tissues, including but not limited to, adipose mesenchymal stem cells, bone marrow mesenchymal stem cells and umbilical cord blood stem cells. The said culture medium can increase the proliferation speed of the stem cells 3-5 times, without any affects on their differentiation potentials. Comparing the said stem cell culture medium to an routine medium, the said medium is not only able to proliferate stem cells derived from different sources more rapidly and achieve more proliferation generations, but also maintain the pluripotency of stem cells.

DETAILED DESCRIPTION OF THE INVENTION

The present invention provides a stem cell culture medium and its applications as well as a stem cell culture method. In order to make the purpose, technical scheme and effect of the present invention more definite and clearer, further details of the invention are explained as follows. However, it should be understood that, the embodiments described herein are used to explain the present invention only, instead of limiting the present invention.

The stem cells culture medium mentioned in the present invention contains no serum, and its formula involves addition of amino acid, vitamins, salts, lipids, cytokines and protein polypeptides, while the present culture method involves materials promoting cell adhesion. Comparing to the routine culture medium, the medium mentioned in present invention is not only able to proliferate stem cells from different sources more rapidly and achieve more generations, but also keep their good proliferation potentials. The said stem cell culture medium is suitable for rapid culturing of stem cells derived from human and mammalian tissues, including but not limited to, adipose mesenchymal stem cells, bone marrow mesenchymal stem cells and umbilical cord blood stem cells.

Specifically, the said stem cell culture medium includes amino acids, vitamins, salts, lipids, cytokines and protein polypeptides;

Wherein, the said amino acids include alanine, arginine, asparagine, aspartic acid, cysteine, glutamic acid, glycine, histidine, isoleucine, leucine, lysine, methionine, phenylalanine, proline, serine, threonine, tryptophan, tyrosine, valine and glutamine;

The said cytokines and protein polypeptides include fibroblast growth factor 1 (FGF1), fibroblast growth factor 2 (FGF2), epidermal growth factor (EGF), platelet derived growth factor (PDGF), insulin (insulin), insulin-like growth factor 1 (IGF1), vascular endothelial growth factor (VEGF), placental growth factor (PGF), Leukocyte inhibitor factor (LIF), stem cell factor (SCF), transferrin (transferrin) and human serum albumin (HSA);

The said vitamins include biotin, choline chloride, D-pantothenic acid sodium, folic acid, inositol, niacinamide, riboflavin, pyridoxine hydrochloride, thiamine hydrochloride, coenzyme Q10, vitamin B12, Putrescine dihydrochloride, vitamin C and vitamin E;

The said lipids include dexamethasone, oleic acid, cholesterol, ethanolamine, linoleic acid, lipoic acid and lipid mixture (Sigma, L5416);

The said trace elements include cobalt chloride, sodium selenite, nickel chloride, manganese chloride, hexaammonium molybdate, aluminum chloride, chromium potassium sulfate, copper sulfate, ferric nitrate, ferrous sulfate and zinc sulfate;

Other small molecules include antioxidants ($\beta$-mercaptoethanol, reduced glutathione), D-glucose, taurine and heparin sodium.

Furthermore, the stem cell culture medium, if counted in 1 liter, comprises the following components:

| Component | Concentration or Amount |
|---|---|
| Ala (Alanine) | 0.01~0.25 mM |
| Arg (Arginine) | 0.4~10 mM |
| Asn (Asparagine) | 0.11~2.75 mM |
| Asp (Asparagic acid) | 0.08~2 mM |
| Cys (Cysteine) | 0.03~0.75 mM |
| Glu (Glutamic acid) | 0.03~0.75 mM |
| Gly (Glycine) | 0.05~1.25 mM |
| His (Histidine) | 0.03~0.75 mM |
| Ile (Isoleucine) | 0.5~12.5 mM |
| Leu (Leucine) | 0.24~6 mM |
| Lys (Lysine) | 0.2~5 mM |
| Met (Methionine) | 0.12~3 mM |
| Phe (Phenylalanine) | 0.21~5.25 mM |
| Pro (Proline) | 0.004~0.1 mM |
| Ser (Serine) | 0.15~3.5 mM |
| Thr (Threonine) | 0.06~1.5 mM |
| Trp (Tryptophan) | 0.02~0.5 mM |
| Tyr (Tyrosine) | 0.03~0.75 mM |
| Val (Valine) | 0.28~7 mM |
| Gln (Glutamine) | 0.8~20 mM |
| Epidermal growth factor (EGF) | 1-10 µg/L |
| Fibroblast growth factor-1 (FGF1) | 1-10 µg/L |
| Fibroblast growth factor-2 (FGF2) | 1-10 µg/L |
| Insulin-like growth factor 1 (IGF1) | 1-10 µg/L |
| Leukocyte inhibitor factor (LIF) | 1-10 µg/L |
| Platelet derived growth factor (PDGF) | 1-10 µg/L |
| Placental growth factor (PGF) | 1-10 µg/L |
| Stem cell factor (SCF) | 1-10 µg/L |
| Vascular endothelial growth factor (VEGF) | 1-10 µg/L |
| insulin | 1~25 mg/L |
| transferrin | 4~100 mg/L |
| Human serum albumin (HSA) | 0.02~0.5 g/L |
| biotin | 6~150 µM |
| Choline chloride | 12~300 µM |
| Folic acid | 1.2~30 µM |
| Coenzyme Q10 | 0.2~5 µM |
| Dexamethasone | 2~50 nM |
| D-pantothenic acid sodium | 1~25 µM |
| i-Inositol | 14~350 µM |
| Niacinamide | 4~100 µM |
| Pyridoxine hydrochloride | 0.03~0.75 µM |
| Riboflavin | 0.11~2.75 µM |
| Thiamine hydrochloride | 0.11~2.75 µM |
| Vitamin B12 | 0.1~2.5 µM |
| Putrescine Dihydrochloride (Putresicine•2HCl) | 0.1~2.5 µM |
| Vitamin C | 2~50 mg/L |
| Vitamin E | 0.05~1.25 mg/L |
| Heparin sodium | 0.08~2 g/L |
| D-glucose | 3.6~90 mM |
| Reduced glutathione | 0.0002~0.005 mg/L |
| Taurine | 0.00144~0.36 g/L |
| $\beta$-mercaptoethanol (BME) | 0.01~0.25 µg/L |
| Phenol red | 1.62~40.5 mg/L |
| Oleic acid | 0.5~12.5 mg/L |
| Linoleic acid | 0.5~7.5 mg/L |
| Lipoic acid | 0.02~0.5 mg/L |
| Lipid mixture (Sigma, L5416) | 0.2~5 ml/L |
| Cholesterol | 1~25 mg/L |

-continued

| Component | Concentration or Amount |
|---|---|
| Ethanolamine | 12~300 µl/L |
| Sodium Bicarbonate (NaHCO$_3$) | 2.32~58 mM |
| Calcium Chloride (CaCl$_2$) | 0.0168~0.42 mM |
| Potassium Chloride(KCl) | 0.832~20.8 mM |
| Magnesium Chloride (MgCl$_2$) | 0.06~1.5 mM |
| Magnesium Sulfate (MgSO$_4$) | 0.0814~2.035 mM |
| Sodium Chloride(NaCl) | 24.122~603.55 mM |
| Sodium Dihydrogen Phosphate Monohydrate(NaH$_2$PO$_4$•H$_2$O) | 0.0906~2.265 mM |
| Sodium Phosphate Dibasic(Na$_2$HPO$_4$) | 0.1~2.5 mM |
| Sodium pyruvate | 0.1~2.5 mM |

The said culture medium provided in the present invention is suitable for rapid culture of stem cells derived from human and mammalian tissues, including but not limited to, adipose mesenchymal stem cells, bone marrow mesenchymal stem cells and umbilical cord blood stem cells. The said culture medium can increase 3-5 times of the proliferation speed of the stem cells, but without any effects on their differentiation potentials.

As good as those cultured in any routine culture medium, stem cells cultured in the said cell culture medium provided in the present invention can differentiate into functional cells successfully, which include, but not limited to, adipose cells, cartilage cells, nerve cells, retinal pigment epithelial cells and retinal photoreceptor cells. On the one hand, stem cells cultured in the said culture medium provided in the present invention are the same as those cultured in routine culture medium, providing good protections to degenerative tissues or organs, after cell transplantations; On the other hand, stem cells cultured in the said culture medium provided in the present invention are the same as those cultured in routine culture medium can restore their original functions after cell transplantations.

The present invention also provides applications to the said stem cell culture medium, the said stem cell culture medium is used to culture stem cells, include but not limited to, stem cells derived from human and mammalian (such as mouse, rat and rabbit). The said stem cells can be separated from tissues or organs. The said tissues and organs include but not limited to the bone marrow, umbilical cord, adipose tissues, brain tissues, retina, heart, liver, lung and skin.

When culturing stem cells in the said stem cell culture medium provided in the present invention, because there is no materials promoting cell adhesion contained in the said culture medium provided in the present invention, such as any one or a mixture of collagen, gelatin, polylysine, fibronectin, laminin and glassy surface adhesion protein. Since the culture medium with blood serum contains these materials, there is no need to add them in; while the said stem cells culture medium without blood serum as provided in the present invention, contains no these materials, thus, before culturing stem cells, coat the culture dish with these materials promoting cells adhesive, then add the said culture medium and stem cells in sequence, and culture stem cells in a normal culture way.

Further descriptions to the present invention are stated below through specific embodiments, In the examples 1-6, wherein, the stem cell culture medium adopted here, counted in 1 liter, comprises the following components:

| Component | Concentration or amount |
|---|---|
| Ala (Alanine) | 0.05 mM |
| Arg (Arginine) | 2.00 mM |
| Asn (Asparagine) | 0.55 mM |
| Asp (Aspartic Acid) | 0.4 mM |
| Cys (Cysteine) | 0.15 mM |
| Glu (Glutamic Acid) | 0.15 mM |
| Gly (Glycine) | 0.25 mM |
| His (Histidine) | 0.15 mM |
| Ile (Isoleucine) | 2.50 mM |
| Leu (Leucine) | 1.20 mM |
| Lys (Lysine) | 1.00 mM |
| Met (Methionine) | 0.60 mM |
| Phe (Phenylalanine) | 1.05 mM |
| Pro (Proline) | 0.02 mM |
| Ser (Serine) | 0.70 mM |
| Thr (Threonine) | 0.30 mM |
| Trp (Tryptophan) | 0.10 mM |
| Tyr (Tyrosine) | 0.15 mM |
| Val (Valine) | 1.4 mM |
| Gln (Glutamine) | 4 mM |
| Epidermal growth factor (EGF) | 1-10 µg/L |
| Fibroblast growth factor 1 (FGF1) | 1-10 µg/L |
| Fibroblast growth factor2 (FGF2) | 1-10 µg/L |
| Insulin-like growth factor 1 (IGF1) | 1-10 µg/L |
| Leukocyte inhibitor factor (LIF) | 1-10 µg/L |
| Platelet derived growth factor (PDGF) | 1-10 µg/L |
| Placenta growth factor (PGF) | 1-10 µg/L |
| Stem cell factor (SCF) | 1-10 µg/L |
| Vascular endothelial growth factor (VEGF) | 1-10 µg/L |
| Insulin | 5 mg/L |
| Transferrin | 20 mg/L |
| Human serum albumin (HSA) | 0.1 g/L |
| Biotin | 30 µM |
| Choline chloride | 60 µM |
| Folic acid | 6 µM |
| Coenzyme Q10 | 1 µM |
| Dexamethasone | 10 nM |
| D-pantothenic acid sodium | 5 µM |
| Inositol | 70 µM |
| Niacinamide | 20 µM |
| Pyridoxine hydrochloride | 0.15 µM |
| Riboflavin | 0.55 µM |
| Thiamine hydrochloride | 0.55 µM |
| Vitamin B12 | 0.5 µM |
| Putrescine Dihydrochloride (Putresicine•2HCl) | 0.5 µM |
| Vitamin C | 10 mg/L |
| Vitamin E | 0.25 mg/L |
| Heparin sodium | 0.4 g/L |
| D-glucose | 18 mM |
| Reduced glutathione | 0.001 mg/L |
| Taurine | 0.0072 g/L |
| β-mercaptoethanol (BME) | 0.05 µg/L |
| Phenol red | 8.1 mg/L |
| Oleic acid | 2.50 mg/L |
| Linoleic acid | 1.5 mg/L |
| Lipoic acid | 0.1 mg/L |
| Lipid mixture (Sigma, L5416) | 1 ml/L |
| Cholesterol | 5 mg/L |
| Ethanolamine | 60 µl/L |
| Sodium bicarbonate (NaHCO$_3$) | 11.6 mM |
| Calcium chloride (CaCl$_2$) | 0.084 mM |
| Potassium chloride(KCl) | 4.16 mM |
| Magnesium chloride (MgCl$_2$) | 0.3 mM |
| Magnesium sulfate (MgSO$_4$) | 0.407 mM |
| Sodium chloride(NaCl) | 120.61 mM |
| Sodium dihydrogen phosphate monohydrate(NaH$_2$PO$_4$•H$_2$O) | 0.453 mM |
| Sodium phosphate dibasic(Na$_2$HPO$_4$) | 0.5 mM |
| Sodium pyruvate | 0.5 mM |

Embodiment 1

Acceleration of Stem Cell Proliferations

Routine culture medium formulas for stem cells are: DMEM/F12 basic culture medium, 10% fetal bovine serum (FBS). In order to compare and check up the effects to proliferation rate of stem cells cultured in the said medium described in the present invention, human stem cells derived from three tissues, lipid, bone marrow and umbilical cord (ADSC, BMSC, UMBSC) are selected, to execute the cell culture experiments in vitro.

Figure 1A:
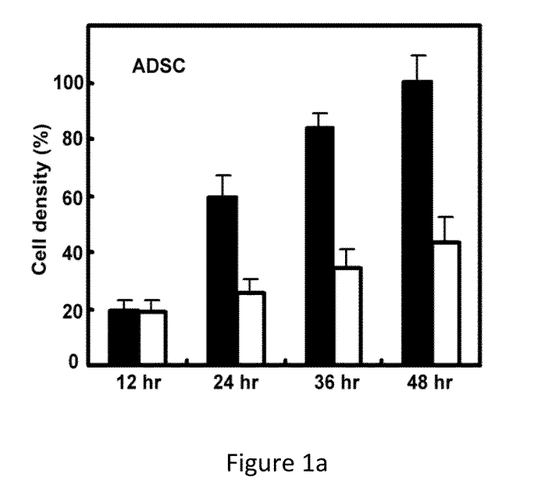
FIG. 1a is a schematic view of test results for proliferation speed of ADSC stem cells cultured in the said culture medium as described in the present invention and in the routine culture medium as shown in the example 1 of the embodiment of the present invention.
Figure 1B:
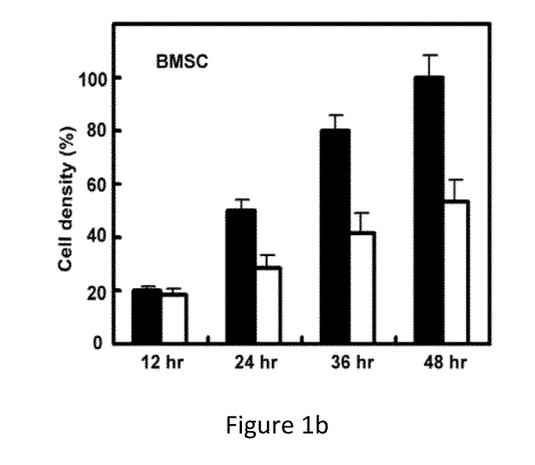
FIG. 1b is a schematic view of test results for proliferation speed of BMSC stem cells cultured in the said culture medium as described in the present invention and in the routine culture medium as shown in example 1 of the embodiment of the present invention.
Figure 1C:
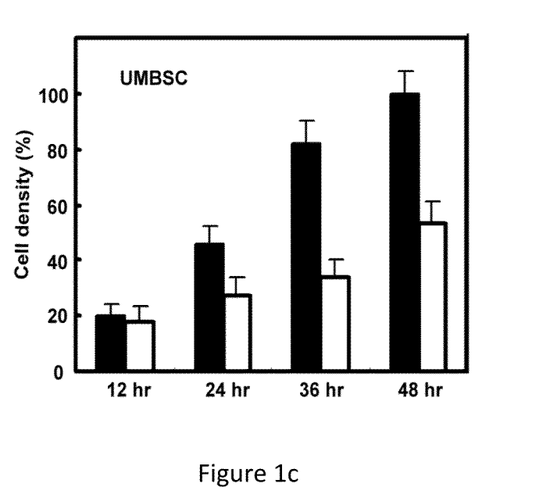
FIG. 1c is a schematic view of test results for proliferation speed of UMBSC stem cells cultured in the said culture medium as described in the present invention and in the routine culture medium as shown in example 1 of the embodiment of the present invention.
Figure 2:
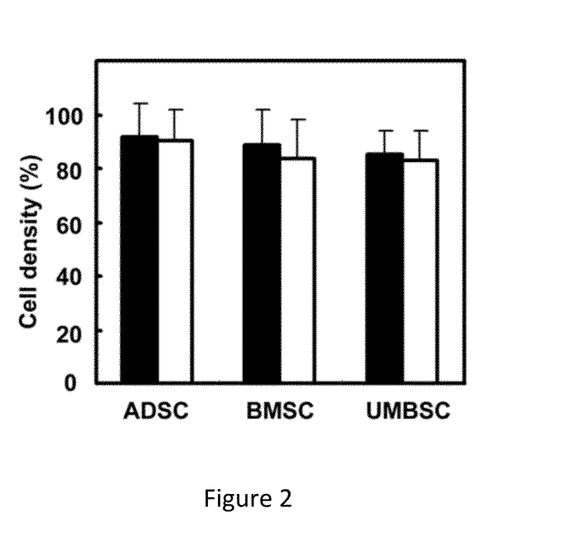
FIG. 2 is a schematic view of test results for the differentiation potential into chondrocytes in vitro for ADSC, BMSC and UMBSC stem cells cultured in the said culture medium as described in the present invention and in the routine culture medium as shown in the example 2 of the embodiment of the present invention.
Figure 3:
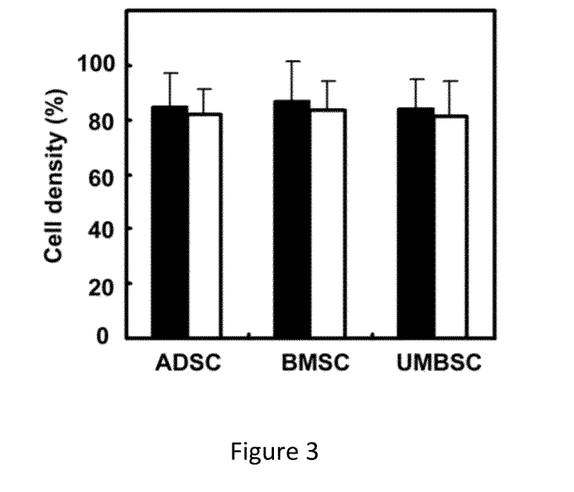
FIG. 3 is a schematic view of test results for the differentiation potential into adipocytes in vitro for ADSC, BMSC and UMBSC stem cells cultured in the said culture medium as described in the present invention and in the routine culture medium as shown in the example 3 of the embodiment of the present invention.

Cell inoculation density is controlled in between 10-20%. Before inoculation, culture dishes are processed with cell adhesion promotion materials for 2 hours in room temperature, or overnight when kept in 4° C. After inoculation, add culture medium in and start cell culture (37° C., 5% $CO_2$). Measure the cell density every 12 hours by MTT method. Test results are shown in FIGS. 1~3, the stem cells cultured in the medium described in present invention (solid cylindrical) showed a more rapid proliferation speed than that showed by those cells cultured in routine culture medium with serum (hollow cylindrical). Data showed are the average of three independent experiments ±SEM (P<0.001). Study results showed that, the time of reaching 100% cell density is greatly shortened in the stem cell culture medium described in present invention, comparing to the routine culture medium with serum added.

Embodiment 2

Analysis of the Differentiation Potential of Mesenchymal Stem Cells into Chondrocytes In Vitro after Proliferations In order to check the effects to stem cells differentiation potential after proliferating for 10 generations in the said culture medium as described in the present invention, chondrogenic differentiation experiments are executed after proliferations of the human stem cells derived from three tissues, lipid, bone marrow and umbilical cord (ADSC, BMSC, UMBSC), following the methods described in literatures (Estes B T et al. Nat Protoc 2010; 5: 1294-1311; Awad H A et al., Biomaterials. 2004 July; 25 (16):3211-22; Cheng N C et al., Tissue Eng Part A. 2009 February; 15 (2):231-41). When the stem cells grow to the appropriate density (20-80% cell density), chondrogenic induction medium (DMEM/F12 culture medium with 1% FBS, 10 µg/L TGF-β 1, 50 nM of vitamin C, 6.25 mg/L insulin and 1% double antibody) is added in. Change the solution every day for a total of 2-3 weeks inducing period. Alcian blue stains after successful induction. The formula of 1% alcian blue staining solution used is: Weighing 0.1 g alcian blue, dissolved in 10 ml 3% acetic acid solution, after the precipitation is dissolved, filter with 0.22 µm strainer before use. The detailed staining method is: Wash with PBS after sucking the cell culture medium off, add 4% paraformaldehyde solution in and fix for 30 minutes, then wash 2-3 times with PBS. Add newly made alcian blue staining solution in and stain for 40 minutes, wash with PBS 3 times (2 minutes each time), and observe the sample under microscope. Count the positive cells after staining the cartilage cells. The statistical results are shown in FIG. 2. The ratio of stem cells differentiating into chondrocytes cultured in the medium described in the present invention (solid cylindrical) and that cultured in the routine culture medium with serum (hollow cylindrical) is about 90% in both cases, therefore both are shown similar promotion ability for stem cells differentiating into chondrocytes. Data used are the average ±SEM of three independent experiments. The results have shown that, the ratio of stem cells differentiating into chondrocytes when cultured in the medium described in the present invention is similar to that of stem cells cultured in routine stem cell culture medium. Thus stem cells cultured in the medium described in the present invention can keep their potentials of differentiating into chondrocytes.

Embodiment 3

Analysis of the Differentiation Potential into Adipose Cells

In order to further check the effects to stem cell differentiation potential after proliferating for 10 generations in the said culture medium as described in present invention, in the current example, adipocytes differentiation experiments are executed after proliferations of the human stem cells derived from three tissues, lipid, bone marrow and umbilical cord (ADSC, BMSC, UMBSC), following the methods of ADSC differentiation into lipid inducing cells and the oil red O staining methods as described in the literatures (Yu G et al., Methods in Molecular Biology, 2011, Volume 702, Part 3, 193-200; Bunnell B A et al., Methods. Volume 45, Issue 2, June 2008, Pages 115-120; Gimble J M & Guilak F. Cytotherapy. 2003, Vol. 5, No. 5, Pages 362-369). Specifically, inducing the stem cells with adipogenic culture medium when their density is around 80%, herein, the adipogenic culture medium formula is: DMEM/F12 medium with 1% FBS, 1 µM dexamethasone, 200 µM indomethacin, 0.5 nM 3-isobutyl 1-methylxanthine (IBMX), 10 µg/ml insulin. Change the liquid every two days, and after two weeks' inducing, stain with oil red O solution, which is made by oil red O, wherein, oil red O storage solution obtained from below method: 0.5 g oil red O is added into 100 ml isopropanol, filter with 0.22 µm strainer. Oil red O solution obtained from below method: add 6 ml oil red O storage solution into 4 ml distilled water, mix evenly. The detailed method is: suck the culture medium off and wash twice with PBS after success adipogenic induction; stain for 1 hour with newly made oil red O staining solution; remove the staining solution, wash 3 times with PBS, 2 minutes each time, and observe under microscope. Count the positive cells after staining the adipose cells. The statistic results are shown in FIG. 3, the ratio of stem cells differentiation into adipose cells, cultured in the culture medium described in the present invention (solid cylindrical) and in the routine culture medium with serum (hollow cylindrical) both are around 80-90%, and both culture medium have shown similar promotion ability for stem cells differentiating into adipose cells. All data are the average ±SEM of three independent experiments. The results have shown that, stem cells cultured in the said medium as described in the present invention own the similar ratio of differentiation into adipose cells as those cultured in routine culture medium with serum. Thus stem cells cultured in the medium described in the present invention can keep their potentials of differentiating into adipose cells.

Embodiment 4

Analysis of the Differentiation Potential into Neuroblasts

Figure 4:
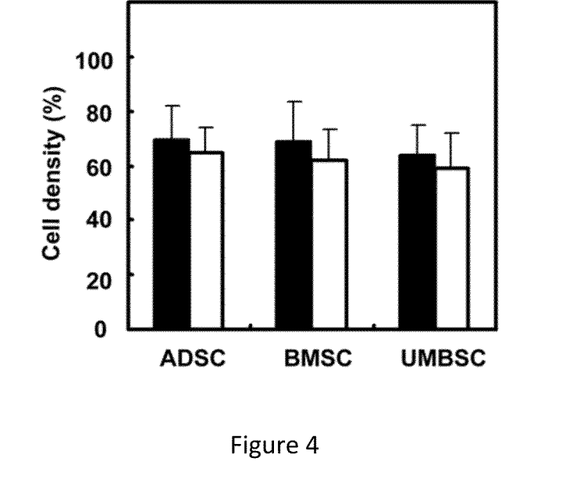
FIG. 4 is a schematic view of test results for the differentiation potential into neuroblast cells in vitro for ADSC, BMSC and UMBSC stem cells cultured in the said culture medium as described in the present invention and in the routine culture medium as shown in example 4 of the embodiment of the present invention.

In order to further check the effects to stem cells differentiation potential after proliferating in the said culture medium described in the present invention, neuroblasts differentiation experiments are executed after proliferation for 10 generations of the human stem cells derived from three tissues, lipid, bone marrow and umbilical cord (ADSC, BMSC, UMBSC), following the methods described in literature (Wu H et al. Proc Natl Acad Sci USA. 2007 Aug. 21; 104(34): 13821-6.). Specifically, when the stem cells grow to the appropriate density (70-80% cell density) after differentiation induction medium, i.e., DMEM/F12, 10% FBS, 1~2 mM BME, is added in. Suck the culture medium off after 24 hours, wash twice with PBS. Change the medium into DMEM, 1~4 mM BME, process for 1~5 hours, suck the culture medium off, change to N2 culture medium with 20 ng bFGF, resume culturing. The ratio of additive DMEM/F12:N2 is 1:1. Inducing differentiation into neuroblast cells for 30 minutes to 10 days. Immunocytochemistry examinations are executed directly in the culture dishes. Neuron specific markers that need to be checked include the neuron specific enolase (NSE) and neurofilament (NF). First, wash off the culture medium with 0.01 mol/L PBS, fix with 4% paraformaldehyde for 15 minutes. Wash 3 times by PBS, 5 minutes each. Process with 0.25% Triton X-100 for 15 minutes; wash 3 times by PBS, 5 minutes each; process with primary antibody containing 1% sheep serum for 1.5 hours in 37° C., and keep in 4° C. overnight; Wash 3 times with PBS, 5 minutes each; add in FITC-conjugated rabbit anti-mouse IgG secondary antibody; incubate for 1 hour in 37° C.; Wash 3 times with PBS, 5 minutes each; Directly take observation and photography under fluorescence microscope after fluorescent staining. Stain with ABC staining method following its manual. Count positive cells after staining the nerve cell markers. The statistic results are shown in FIG. 4, the ratio of stem cells differentiation into neuroblasts, cultured in the medium described in the present invention (solid cylindrical) and in the routine medium with serum (hollow cylindrical) is around 60-70%, and both culture mediums have shown similar promotion ability for stem cells differentiating into neuroblasts. Data are the average ±SEM of three independent experiments. The results have shown that, stem cells cultured in the said medium as described in the present invention own the similar ratio of differentiation into neuroblasts as those cultured in routine culture medium with serum. Therefore, stem cells cultured in the medium described in the present invention can keep their potentials of differentiating into neuroblasts.

Embodiment 5

Analysis of the Differentiation Potential into Retinal Epithelial Cells

Figure 5:
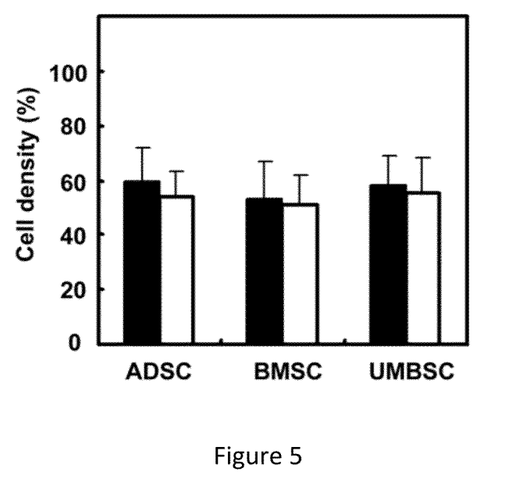
FIG. 5 is a schematic view of test results for the differentiation potential into retinal pigment epithelial cells in vitro for ADSC, BMSC and UMBSC stem cells cultured in the said culture medium of present invention and in the routine culture medium as shown in the example 5 of the embodiment of the present invention.

In order to further check the effects to stem cells differentiation potential after proliferating in the said culture medium described in present invention, retina pigment epithelial cell (RPE) differentiation experiments are executed after proliferations for 10 generations of the human stem cells derived from three tissues, lipid, bone marrow and umbilical cord (ADSC, BMSC, UMBSC), following the methods described in literature (Osakada F et al., Nat. Biotechnol. 2008 February; 26 (2): 215-24.). Count positive cells after staining the RPE cell markers. The statistic results are shown in FIG. 5, the ratio of stem cells differentiation into RPE cells, cultured in the medium described in the present invention (solid cylindrical) and in the routine medium with serum (hollow cylindrical) is around 55-70% in both cases, and both medium have shown similar promotion ability for stem cells differentiating into RPE cells. The results have shown that, stem cells cultured in the said medium as described in the present invention own the similar ratio of differentiation into RPE cells as those cultured in routine culture medium with serum. Thus stem cells cultured in the medium described in the present invention can keep their potentials of differentiating into RPE cells.

Embodiment 6

Figure 6:
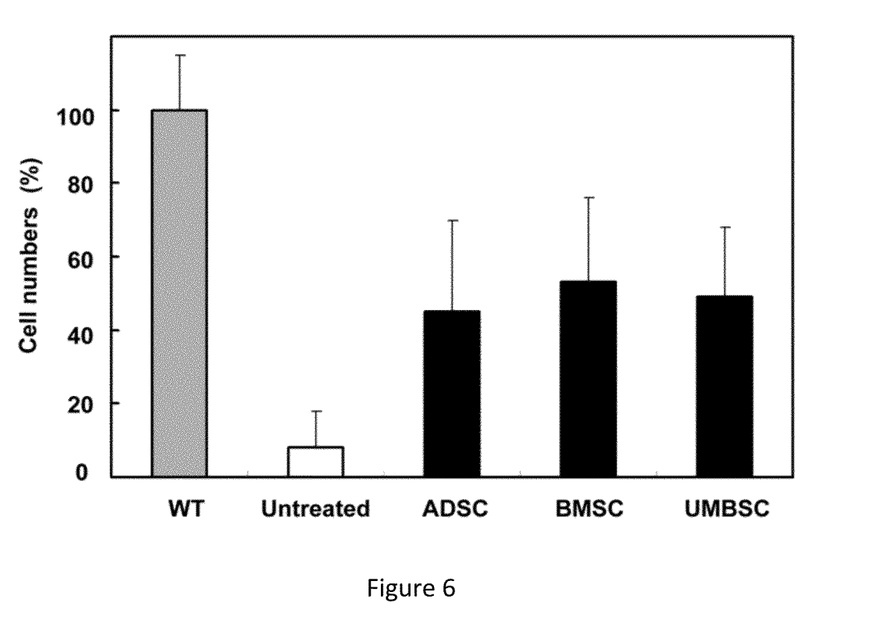
FIG. 6 is a schematic view of test results for ADSC, BMSC, UMBSC cultured in the said culture medium of the present invention to photoreceptor cells retinal degenerative model after implantations.

Protective Effect on Stem Cells to the Cell Degeneration Model after Proliferation In order to detect the treatment effect on stem cells to degenerative diseases after proliferation in the said culture medium described in present invention, the mouse model on retinal photoreceptor cells retinal degenerative disease (rd1) is selected (Bowes C et al., Nature. 1990 Oct. 18; 347 (6294): 677-80). After implanting the post-10-generation-proliferation human stem cells (ADSC, BMSC, or UMBSC) into retina, histological examination of the number of photoreceptor cells, to decide their protective effects to retinal photoreceptor cells, is executed. The results are shown in FIG. 6, the number of photoreceptor cells of Rd1 mouse rises from less than 5% to over 40%, after 1 month treatment with stem cells. Thus the stem cells still keep their protective ability to degenerative cells after cultured in the said medium described in present invention. Data are the average ±SEM (P<0.001) of three independent experiments. The study shows, the photoreceptor cells degeneration speed slows down significantly after implanting the stem cells and, stem cells are still protecting the retinal cells after proliferation in the culture medium described in the present invention.

In conclusion, stem cells cultured through the culture medium described in the present invention are the same as those cultured through routine culture medium, they are able to differentiate into functional cells, which include, but not limited to adipose cells, cartilage cells, nerve cells, myocardial cells, retinal pigment cells and retinal photoreceptor cells under appropriate conditions. Moreover, implantation of stem cells has a good protection effect on degenerative tissue or organ models, which include, but not limited to, a genetic mutation modified retinal degenerative model. And the examination results have shown that, the stem cell culture medium without serum as described in the present invention suits better than the routine culture medium used in stem cell culture.

It should be understood that, the application of the present invention is not limited to the above examples listed. It will be possible for a person skilled in the art to make modifications or replacements according to the above description, which shall all fall within the scope of the appended claims of the present invention.

The invention claimed is:
1. A stem cell culture medium, wherein, the culture medium contains no serum, and the stem cell culture medium contains amino acids, vitamins, salts, lipids, cytokines and protein polypeptides;
  the amino acids include Alanine, Arginine, Asparagine, Aspartic acid, Cysteine, Glutamic acid, Glycine, Histidine, Isoleucine, Leucine, Lysine, Methionine, Phenylalanine, Proline, Serine, Threonine, Tryptophan, Tyrosine, Valine, and Glutamine;
  the cytokines and protein polypeptides include fibroblast growth factor 1, fibroblast growth factor 2, epidermal growth factor, platelet-derived growth factor, insulin, insulin-like growth factor 1, vascular endothelial cell growth factor, placenta growth factor, leukocyte inhibitor factor, stem cell factor, transferrin and human serum albumin;

the vitamins include, biotin, choline chloride, D-pantothenic acid sodium, folic acid, inositol, niacinamide, riboflavin, pyridoxine hydrochloride, thiamine hydrochloride, coenzyme Q10, vitamin B12, putrescine dihydrochloride, vitamin C and vitamin E;

the lipids include dexamethasone, oleic acid, cholesterol, monoethanolamine, linoleic acid, lipoic acid and lipid mixtures;

the salts include sodium bicarbonate, calcium chloride, potassium chloride, magnesium chloride, magnesium sulfate, sodium chloride, monohydrate sodium dihydrogen phosphate, disodium hydrogen phosphate, and sodium pyruvate;

the stem cell culture medium further includes antioxidant, D-glucose, taurine, and sodium heparin; and the culture medium, counted in 1 liter, includes the following components:

| T1 | |
|---|---|
| Alanine | 0.01-0.25 mM |
| Arginine | 0.4-10 mM |
| Asparagine | 0.11-2.75 mM |
| Aspartic acid | 0.03-0.75 mM |
| Cysteine | 0.03-0.75 mM |
| Glutamic acid | 0.03-0.75 mM |
| Glycine | 0.05-1.25 mM |
| Histidine | 0.03-0.75 mM |
| Isoleucine | 0.5-12.5 mM |
| Leucine | 0.24-6 mM |
| Lysine | 0.2-5 mM |
| Methionine | 0.12-3 mM |
| Phenylalanine | 0.21-5.25 mM |
| Proline | 0.004-0.1 mM |
| Serine | 0.15-3.5 mM |
| Threonine | 0.06-1.5 mM |
| Tryptophan | 0.02-0.5 mM |
| Tyrosine | 0.03-0.75 mM |
| Valine | 0.28-7 mM |
| Glutamine | 0.8-20 mM |
| Epidermal growth factor | 1-10 µg/L |
| Fibroblast growth factor 1 | 1-10 µg/L |
| Fibroblast growth factor 2 | 1-10 µg/L |
| Insulin-like growth factor 1 | 1-10 µg/L |
| Leukocyte inhibitor factor | 1-10 µg/L |
| Platelet derived growth factor | 1-10 µg/L |
| Placenta growth factor | 1-10 µg/L |
| Stem cell factor | 1-10 µg/L |
| Vascular endothelial growth factor | 1-10 µg/L |
| Insulin | 1-25 mg/L |
| Transferrin | 4-100 mg/L |
| Human serum albumin | 0.02-0.5 g/L |
| Biotin | 6-150 µM |
| Choline chloride | 12-300 µM |
| Folic acid | 1.2-30 µM |
| Coenzyme Q10 | 0.2-5 µM |
| Dexamethasone | 2-50 nM |
| D-pantothenic acid sodium | 1-25 µM |
| Inositol | 14-350 µM |
| Nicotinamide | 4-100 µM |
| Pyridoxine hydrochloride | 0.03-0.75 µM |
| Riboflavin | 0.11-2.75 µM |
| Thiamine hydrochloride | 0.11-2.75 µM |
| Vitamin B12 | 0.1-2.5 µM |
| Putrescine dihydrochloride | 0.1-2.5 µM |
| Vitamin C | 2-50 mg/L |
| Vitamin E | 0.05-1.25 mg/L |
| Heparin sodium | 0.08-2 g/L |
| D-glucose | 3.6-90 mM |
| Reduced glutathione | 0.0002-0.005 mg/L |
| Taurine | 0.00144-0.36 g/L |
| β-mercaptoethanol | 0.01-0.25 µg/L |
| Phenol red | 1.62-40.5 mg/L |
| Oleic acid | 0.5-12.5 mg/L |
| Linoleic acid | 0.5-7.5 mg/L |
| Lipoic acid | 0.02-0.5 mg/L |
| Lipid mixtures | 0.2-5 ml/L |
| Cholesterol | 1-25 mg/L |
| Ethanolamine | 12-300 µl/L |
| Sodium bicarbonate | 11.6 mM |
| Calcium chloride | 0.084 mM |
| Potassium chloride | 4.16 mM |
| Magnesium chloride | 0.3 mM |
| Magnesium sulfate | 0.407 mM |
| Sodium chloride | 120.61 mM |
| Sodium dihydrogen phosphate monohydrate | 0.453 mM |
| Sodium phosphate dibasic | 0.5 mM |
| Sodium pyruvate | 0.1-2.5 mM. |

2. The stem cell culture medium of claim 1, wherein, the culture medium, counted in 1 liter, includes the following components:

| | |
|---|---|
| Alanine | 0.05 mM |
| Arginine | 2 mM |
| Asparagine | 0.55 mM |
| Aspartic acid | 0.4 mM |
| Cysteine | 0.15 mM |
| Glutamic acid | 0.15 mM |
| Glycine | 0.25 mM |
| Histidine | 0.15 mM |
| Isoleucine | 2.50 mM |
| Leucine | 1.20 mM |
| Lysine | 1.00 mM |
| Methionine | 0.60 mM |
| Phenylalanine | 1.05 mM |
| Proline | 0.02 mM |
| Serine | 0.70 mM |
| Threonine | 0.30 mM |
| Tryptophan | 0.10 mM |
| Tyrosine | 0.15 mM |
| Valine | 1.4 mM |
| Glutamine | 4 mM |
| Epidermal growth factor | 1-10 µg/L |
| Fibroblast growth factor-1 | 1-10 µg/L |
| Fibroblast growth factor-2 | 1-10 µg/L |
| Insulin-like growth factor 1 | 1-10 µg/L |
| Cytokines | 1-10 µg/L |
| Platelet derived growth factor | 1-10 µg/L |
| Placental growth factor | 1-10 µg/L |
| Stem cell factor | 1-10 µg/L |
| Vascular endothelial growth factor | 1-10 µg/L |
| Insulin | 5 mg/L |
| Transferrin | 20 mg/L |
| Human serum albumin | 0.1 g/L |
| Biotin | 30 µM |
| Choline chloride | 60 µM |
| Folic acid | 6 µM |
| Coenzyme Q10 | 1 µM |
| Dexamethasone | 10 nM |
| D-pantothenic acid sodium | 5 µM |
| Inositol | 70 µM |
| Nicotinamide | 20 µM |
| Pyridoxine hydrochloride | 0.15 µM |
| Riboflavin | 0.55 µM |
| Thiamine hydrochloride | 0.55 µM |
| Vitamin B12 | 0.5 µM |
| Putrescine dihydrochloride | 0.5 µM |
| Vitamin C | 10 mg/L |
| Vitamin E | 0.25 mg/L |
| Heparin sodium | 0.4 g/L |
| D-glucose | 18 mM |
| Reduced glutathione | 0.001 mg/L |
| Taurine | 0.0072 g/L |
| β-mercaptoethanol | 0.05 µg/L |
| Phenol red | 8.1 mg/L |
| Oleic acid | 2.5 mg/L |
| Linoleic acid | 1.5 mg/L |

-continued

| | | |
|---|---|---|
| Lipoic acid | 0.1 | mg/L |
| Lipid mixtures | 1 | ml/L |
| Cholesterol | 5 | mg/L |
| Ethanolamine | 60 | μl/L |
| Sodium bicarbonate | 11.6 | mM |
| Calcium chloride | 0.084 | mM |
| Potassium chloride | 4.16 | mM |
| Magnesium chloride | 0.3 | mM |
| Magnesium sulfate | 0.407 | mM |
| Sodium chloride | 120.61 | mM |
| Sodium dihydrogen phosphate | 0.453 | mM |
| Disodium hydrogen phosphate | 0.5 | mM |
| Sodium pyruvate | 0.5 | mM. |

3. The stem cell culture medium of claim 1, wherein the stem cell culture medium is capable of culturing stem cells.

4. The stem cell culture medium of claim 3, wherein the stem cells include stem cells derived from human and mammal.

5. The stem cell culture medium of claim 3, wherein:
the stem cells are obtained from isolation of various tissues or organs; and
each of the tissues and organs includes bone marrow, umbilical cord, adipose tissue, brain tissue, retina, heart, liver, lung and skin.

6. A method for culturing stem cells, comprising:
growing the stem cells in a stem cell culture medium, wherein:
the culture medium contains no serum, and the stem cell culture medium contains amino acids, vitamins, salts, lipids, cytokines and protein polypeptides;
the amino acids include Alanine, Arginine, Asparagine, Aspartic acid, Cysteine, Glutamic acid, Glycine, Histidine, Isoleucine, Leucine, Lysine, Methionine, Phenylalanine, Proline, Serine, Threonine, Tryptophan, Tyrosine, Valine, and Glutamine;
the cytokines and protein polypeptides include fibroblast growth factor 1, fibroblast growth factor 2, epidermal growth factor, platelet-derived growth factor, insulin, insulin-like growth factor 1, vascular endothelial cell growth factor, placenta growth factor, leukocyte inhibitor factor, stem cell factor, transferrin and human serum albumin;
the vitamins include biotin, choline chloride, D-pantothenic acid sodium, folic acid, inositol, niacinamide, riboflavin, pyridoxine hydrochloride, thiamine hydrochloride, coenzyme Q10, vitamin B12, putrescine dihydrochloride, vitamin C and vitamin E;
the lipids include dexamethasone, oleic acid, cholesterol, monoethanolamine, linoleic acid, lipoic acid and lipid mixtures;
the salts include sodium bicarbonate, calcium chloride, potassium chloride, magnesium chloride, magnesium sulfate, sodium chloride, monohydrate sodium dihydrogen phosphate, disodium hydrogen phosphate, and sodium pyruvate;
the stem cell culture medium further includes antioxidant, D-glucose, taurine, and sodium heparin; and
the stem cell culture medium, counted in 1 liter, includes the following components:

T1
| | | |
|---|---|---|
| Alanine | 0.01-0.25 | mM |
| Arginine | 0.4-10 | mM |
| Asparagine | 0.11-2.75 | mM |
| Aspartic acid | 0.03-0.75 | mM |
| Cysteine | 0.03-0.75 | mM |
| Glutamic acid | 0.03-0.75 | mM |
| Glycine | 0.05-1.25 | mM |
| Histidine | 0.03-0.75 | mM |
| Isoleucine | 0.5-12.5 | mM |
| Leucine | 0.24-6 | mM |
| Lysine | 0.2-5 | mM |
| Methionine | 0.12-3 | mM |
| Phenylalanine | 0.21-5.25 | mM |
| Proline | 0.004-0.1 | mM |
| Serine | 0.15-3.5 | mM |
| Threonine | 0.06-1.5 | mM |
| Tryptophan | 0.02-0.5 | mM |
| Tyrosine | 0.03-0.75 | mM |
| Valine | 0.28-7 | mM |
| Glutamine | 0.8-20 | mM |
| Epidermal growth factor | 1-10 | μg/L |
| Fibroblast growth factor 1 | 1-10 | μg/L |
| Fibroblast growth factor 2 | 1-10 | μg/L |
| Insulin-like growth factor 1 | 1-10 | μg/L |
| Leukocyte inhibitor factor | 1-10 | μg/L |
| Platelet derived growth factor | 1-10 | μg/L |
| Placenta growth factor | 1-10 | μg/L |
| Stem cell factor | 1-10 | μg/L |
| Vascular endothelial growth factor | 1-10 | μg/L |
| Insulin | 1-25 | mg/L |
| Transferrin | 4-100 | mg/L |
| Human serum albumin | 0.02-0.5 | g/L |
| Biotin | 6-150 | μM |
| Choline chloride | 12-300 | μM |
| Folic acid | 1.2-30 | μM |
| Coenzyme Q10 | 0.2-5 | μM |
| Dexamethasone | 2-50 | nM |
| D-pantothenic acid sodium | 1-25 | μM |
| Inositol | 14-350 | μM |
| Nicotinamide | 4-100 | μM |
| Pyridoxine hydrochloride | 0.03-0.75 | μM |
| Riboflavin | 0.11-2.75 | μM |
| Thiamine hydrochloride | 0.11-2.75 | μM |
| Vitamin B12 | 0.1-2.5 | μM |
| Putrescine dihydrochloride | 0.1-2.5 | μM |
| Vitamin C | 2-50 | mg/L |
| Vitamin E | 0.05-1.25 | mg/L |
| Heparin sodium | 0.08-2 | g/L |
| D-glucose | 3.6-90 | mM |
| Reduced glutathione | 0.0002-0.005 | mg/L |
| Taurine | 0.00144-0.36 | g/L |
| β-mercaptoethanol | 0.01-0.25 | μg/L |
| Phenol red | 1.62-40.5 | mg/L |
| Oleic acid | 0.5-12.5 | mg/L |
| Linoleic acid | 0.5-7.5 | mg/L |
| Lipoic acid | 0.02-0.5 | mg/L |
| Lipid mixtures | 0.2-5 | ml/L |
| Cholesterol | 1-25 | mg/L |
| Ethanolamine | 12-300 | μl/L |
| Sodium bicarbonate | 11.6 | mM |
| Calcium chloride | 0.084 | mM |
| Potassium chloride | 4.16 | mM |
| Magnesium chloride | 0.3 | mM |
| Magnesium sulfate | 0.407 | mM |
| Sodium chloride | 120.61 | mM |
| Sodium dihydrogen phosphate monohydrate | 0.453 | mM |
| Sodium phosphate dibasic | 0.5 | mM |
| Sodium pyruvate | 0.1-2.5 | mM. |

7. The method according to claim 6, further comprising:
coating a culture dish with cell adhesion promotion materials;
preparing the stem cell culture medium;
adding the stem cell culture medium to the culture dish; and
adding the stem cells that need to be cultured to the culture dish.

8. The method according to claim 6, wherein, the cell adhesion promotion materials include collagen, gelatin, polylysine, fibronectin, laminin, vibronectin, or a combination thereof.

9. The method according to claim 6, wherein:
the stem cells are obtained by isolating tissues or organs of a human or a mammal; and
each of the tissues and organs includes bone marrow, umbilical cord, adipose tissue, brain tissue, retina, heart, liver, lung, and skin.

10. The method according to claim 7, wherein:
cell inoculation density is controlled between about 10% and about 20%;
before inoculation, the culture dish is processed with the cell adhesion promotion materials for about 2 hours in room temperature, or overnight when maintained at 4° C.; and
after inoculation, the stem cells are added to the stem cell culture medium at about 37° C., under 5% $CO_2$.

11. The method according to claim 10, wherein the stem cells are derived from one or more of lipid, bone marrow and umbilical cord.

12. The method according to claim 6, wherein:
after proliferations for 10 generations of the stem cells derived from at least one of lipid, bone marrow and umbilical cord in the culture medium, the stem cells have similar differentiation potential as stem cells cultured in a culture medium containing serum, wherein the stem cells differentiate into one of chondrocytes, adipose cells, neuroblasts, and retinal epithelial cells.

* * * * *